United States Patent
Nakamura et al.

(10) Patent No.: US 10,478,427 B2
(45) Date of Patent: Nov. 19, 2019

(54) THERAPEUTIC AGENT FOR FIBROSIS AND INHIBITOR OF NUCLEAR TRANSLOCATION OF PHOSPHORYLATED SMAD

(71) Applicant: NATIONAL UNIVERSITY CORPORATION CHIBA UNIVERSITY, Chiba-shi, Chiba (JP)

(72) Inventors: Hiroyuki Nakamura, Chiba (JP); Toshihiko Murayama, Chiba (JP)

(73) Assignee: NATIONAL UNIVERSITY CORPORATION CHIBA UNIVERSITY, Chiba-Shi (JP)

( * ) Notice: Subject to any disclaimer, the term of this patent is extended or adjusted under 35 U.S.C. 154(b) by 34 days.

(21) Appl. No.: 15/641,805

(22) Filed: Jul. 5, 2017

(65) Prior Publication Data

US 2018/0008585 A1    Jan. 11, 2018

(30) Foreign Application Priority Data

Jul. 7, 2016 (JP) .................................. 2016-134880
Jul. 5, 2017 (JP) .................................. 2017-131587

(51) Int. Cl.
*A61K 31/445*    (2006.01)

(52) U.S. Cl.
CPC .................................. *A61K 31/445* (2013.01)

(58) Field of Classification Search
None
See application file for complete search history.

(56) References Cited

U.S. PATENT DOCUMENTS

| 7,973,054 B2 * | 7/2011 | Becq .................... | A61K 31/352 514/315 |
| 2011/0183948 A1* | 7/2011 | Levine ................ | C07D 491/048 514/171 |
| 2015/0118221 A1* | 4/2015 | Chatterjee ............ | A61K 31/401 424/130.1 |

OTHER PUBLICATIONS

Bodas et al., Lactosylceramide-accumulation in lipid-rafts mediate aberrant-autophagy, inflammation and apoptosis in cigarette smoke induced emphysema, Apoptosis, May 2015, 725-39, 20.
Derynck et al., Smad-dependent and Smad-independent pathways in TGF-beta family signalling, Nature Publishing Group, Oct. 9, 2003, 577-84, vol. 425.
King Jr et al., Idiopathic pulmonary fibrosis, Lancet, Dec. 3, 2011, 1949-61, vol. 378.
Kolmakova et al., Platelet derived growth factor recruits lactosylceramide to induce cell proliferation in UDP Gal: GlcCer: beta1 --> 4Galactosyltransferase (GalT-V) mutant Chinese hamster ovary cells, Glycoconjugate Journal, Nov. 22, 2005, 401-7, 22.
Leask, Potential therapeutic targets for cardiac fibrosis: TGFbeta, angiotensin, endothelin, CCN2, and PDGF,partners in fibroblast activation, Circulation Research, Jun. 11, 2010, 1675-80, 106.
Mayo et al., Regulation of astrocyte activation by glycolipids drives chronic CNS inflammation, Nature Medicine, Oct. 20, 2014, 1147-56, vol. 20.
Moustakas, Smad signalling network, Cell Science at a Glance, Sep. 1, 2002, 3355-6, 115.
Nakamura et al., Lactosylceramideinteracts with and activates cytosolic phospholipase A2α, The Journal of Biological Chemistry, Aug. 9, 2013, 23264-72, vol. 288.
Pannu et al., A novel role of lactosylceramide in the regulation of tumor necrosis factor alphamediated proliferation of rat primary astrocytes. Implications for astrogliosis following neurotrauma, The Journal of Biological Chemistry, Apr. 3, 2005, 13742-51, vol. 280.
Raghu et al., An Official ATS/ERS/JRS/ALAT Clinical Practice Guideline: Treatment of Idiopathic Pulmonary Fibrosis. An Update of the 2011 Clinical Practice Guideline, American Journal of Respiratory and Critical Care Medicine, Jul. 15, 2015, pp. e3-e19, vol. 192.
Submission of Certificate of Exception to Loss of Novelty, Submitted to Japan Patent Office Commissioner, Submitted by Applicant on Aug. 1, 2016, including two publications (published on a web site on Mar. 2, 2016 and at a conference on Mar. 11, 2016).
Submission of Certificate of Exception to Loss of Novelty, Submitted to Japan Patent Office Commissioner, Submitted by Applicant on Aug. 1, 2016.
The 89th Annual Meeting of the Japanese Pharmacological Society, published on a web site on Mar. 2, 2016 and at a conference on Mar. 11, 2016.

* cited by examiner

*Primary Examiner* — Sreenivasan Padmanabhan
*Assistant Examiner* — Jody L Karol
(74) *Attorney, Agent, or Firm* — Law Office of Katsuhiro Arai

(57) ABSTRACT

A therapeutic agent for fibrosis, whose active ingredient is constituted by a glucosylceramide synthase inhibitor or lactosylceramide synthase inhibitor, or both, inhibits the nuclear translocation of phosphorylated Smad, thereby treating and preventing fibrosis.

3 Claims, 14 Drawing Sheets

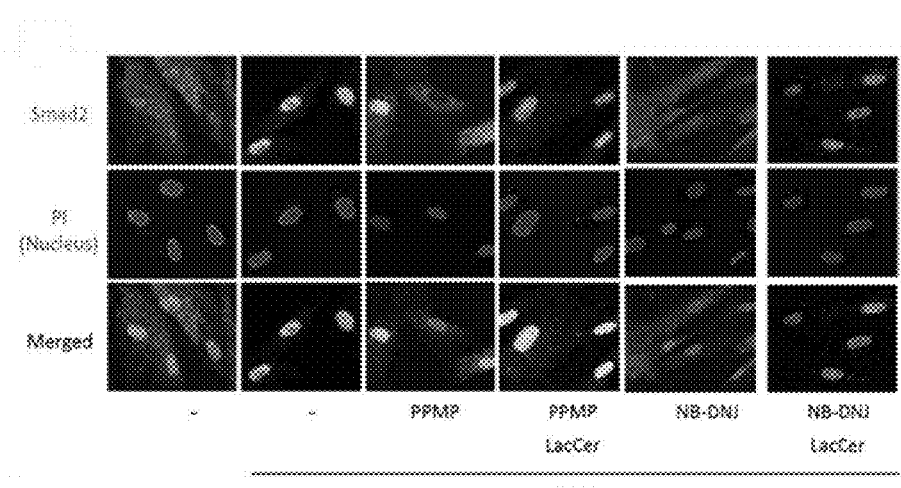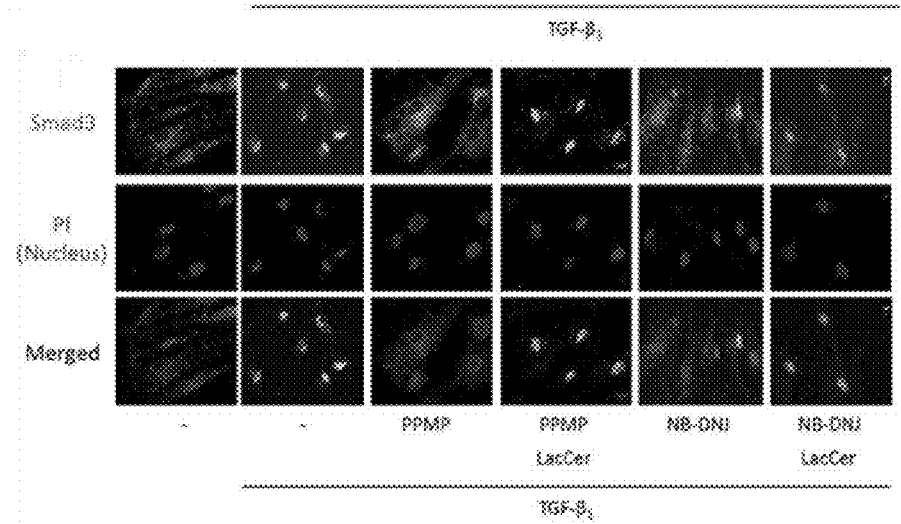

THERAPEUTIC AGENT FOR FIBROSIS AND INHIBITOR OF NUCLEAR TRANSLOCATION OF PHOSPHORYLATED SMAD

BACKGROUND

Field of the Invention

The present invention relates to a therapeutic agent for fibrosis used for treatment or prevention of fibrosis.

Description of the Related Art

Idiopathic interstitial pneumonia is an intractable respiratory disease which is designated as a specific disease in Japan. Among the types of idiopathic interstitial pneumonia, idiopathic pulmonary fibrosis is triggered by unknown causes and has a very poor prognosis in that the median life expectancy of people diagnosed with the disease is two to three years. The incidence rate of idiopathic pulmonary fibrosis is 10 to 20 per 100,000 persons; however, the number of patients potentially suffering from the disease is estimated to be at least ten times that. Key symptoms of idiopathic pulmonary fibrosis includes fibrosing (thickening) of the "interstitium" which is an area that supports the alveolar tissues. Fibrosing of the pulmonary interstitium causes the lung to lose its flexibility and the pulmonary function to decrease, and this in turn prevents smooth exchange of gases and results in breathing difficulty, dry cough, etc.

What causes idiopathic pulmonary fibrosis is not clear; however, smoking has been cited as a risk factor. It has been confirmed that, in the pulmonary tissues of patients suffering from idiopathic pulmonary fibrosis, fibroblast cells and myofibroblast cells that constitute the interstitium aggregate and form foci (Non-patent Literature 1). Also, this formation of foci is understood as the result of complex actions of various types of inflammatory cytokines.

In Japan, pirfenidone and nintedanib have been approved as drugs to treat idiopathic pulmonary fibrosis.

Pirfenidone suppresses the production of inflammatory cytokines (TNF-α, IL-1, IL-6, etc.), while enhancing the production of an anti-inflammatory cytokine (IL-10). It also suppresses the production of growth factors (TGFβ1, b-FGF, PDGF) involved in the formation of fibrosis. Furthermore, the drug suppresses the growth of fibroblast cells and also suppresses the production of collagen. Pirfenidone is considered to have anti-fibrotic action based on the combination of the aforementioned actions; however, the target molecules of pirfenidone are not yet clear.

Nintedanib is a low-molecular-weight tyrosine kinase inhibitor that targets the platelet-derived growth factor receptors (PDGFR) α, β, fibroblast growth factor receptors (FGFR) 1, 2, 3, and vascular endothelial growth factor receptor (VEGFR); to be specific, nintedanib exhibits anti-fibrotic action by inhibiting the growth and migration of fibroblast cells.

However, it has been reported that, while pirfenidone and nintedanib improve the forced vital capacities of patients suffering from idiopathic pulmonary fibrosis, they cannot extend the survival periods of these patients (Non-patent Literature 2).

As a result, it is desired that a new approach be adopted to develop treatment drugs for the disease.

Transforming growth factor-β (TGFβ) is a protein produced in almost all cells in the kidneys, bone marrow, platelets, etc.; it is a cytokine that exhibits various bioactivities such as controlling the growth and differentiation of cells, promoting the growth of osteoblast cells and mesenchymal cells, and promoting the synthesis of collagen, among others. There are five subtypes of TGFβ (β1 to β5), of which the three types of β1, β2 and β3 are present in mammals.

TGFβ1 reportedly plays an important role in the fibrosing of tissues found in idiopathic pulmonary fibrosis, etc. (Non-patent Literatures 1, 3). TGFβ1 is also known as a molecule deeply involved in the healing of wounds, and excessive action of TGFβ1 in tissues is considered to play a significant role in fibrosing. In its relationship with the pulmonary interstitium, TGFβ1 is also known to differentiate fibroblast cells into myofibroblast cells and induce the expression of collagen, fibronectin and other extracellular matrixes as well as α-smooth muscle actin (αSMA), which is a characteristic protein found in myofibroblast cells. It should be noted that αSMA is a fibrosis marker protein.

TGFβ1 binds with a TGFβ receptor as a dimeric ligand. The transcription factor Smad is known as a characteristic molecule that plays the most prominent role in the TGFβ1 signals (Non-patent Literatures 4, 5). Smad has the MH1 domain which is involved in nuclear translocation and DNA binding, and the MH2 domain which is involved in transcriptional activity and binding with other molecules, on the N-terminal side and the C-terminal side, respectively. When Smad is in an inactive state, its MH1 domain and MH2 domain bind together in the molecule; once the TGFβ receptor is activated, however, the SXSS motif present at the C-terminal of the MH2 domain of Smad2/3 is phosphorylated. Then, Smad2/3 form a complex with Smad4 via the MH2 domain (this complex is hereinafter referred to as "phosphorylated Smad"), and this phosphorylated Smad translocates into the nucleus and binds with DNA via the MH1 domain, interacts with various transcription factors, and controls the transcription of various target genes including αSMA.

In the intracellular transmission of various signals including TGFβ1, a lipid raft on cellular membrane acts as a scaffold on which the receptor and the intracellular signal molecule meet. Lipid rafts contain an abundance of glycosphingolipids consisting of ceramides to which sugar chains are attached. There are hundreds of different types of glycosphingolipid molecules that are largely divided into those based on the galactosylceramide matrix constituted by a ceramide to which galactose is attached, and others based on the lactosylceramide matrix constituted by a ceramide to which lactose (disaccharide constituted by glucose and galactose) is attached. Lactosylceramide is synthesized via glucosylceramide which is constituted by a ceramide to which glucose is attached.

It is reported that lipid raft regions containing an abundance of lactosylceramide play a role in the transmission of inflammatory signals (Non-patent Literatures 6 to 10).

However, function of lactosylceramide as a TGFβ1 signal transmission molecule has not been reported, and the relationship of lactosylceramide and TGFβ1 signals is not known.

BACKGROUND ART LITERATURES

[Non-patent Literature 1] King T E Jr, Pardo A, Selman M. Idiopathic pulmonary fibrosis. Lancet. 2011 Dec. 3; 378 (9807): 1949-61.

[Non-patent Literature 2] Ganesh Raghu, Bram Rochwerg, Yuan Zhang, Carlos A. Cuello Garcia, Arata Azuma, Juergen Behr, Jan L. Brozek, Harold R. Collard, William Cunningham, Sakae Homma, Takeshi Johkoh, Fernando J. Martinez, Jeffrey Myers, Shandra L. Protzko, Luca Richeldi, David Rind, Moises Selman, Arthur Theodore, Athol U. Wells, Henk Hoogsteden, and Holger J. Schunemann "An Official ATS/ERS/JRS/ALAT Clinical Practice Guideline: Treatment of Idiopathic Pulmonary Fibrosis. An Update of the 2011 Clinical Practice Guideline", American Journal of Respiratory and Critical Care Medicine, Vol. 192, No. 2 (2015), pp. e3-e19.

[Non-patent Literature 3] Leask A. Potential therapeutic targets for cardiac fibrosis: TGFbeta, angiotensin, endothelin, CCN2, and PDGF, partners in fibroblast activation. Circ Res. 2010 Jun. 11; 106 (11): 1675-80.

[Non-patent Literature 4] Moustakas A. Smad signalling network. J Cell Sci. 2002 Sep. 1; 115 (Pt 17): 3355-6.

[Non-patent Literature 5] Derynck R, Zhang Y E. Smad-dependent and Smad-independent pathways in TGF-beta family signalling. Nature. 2003 Oct. 9; 425 (6958): 577-84.

[Non-patent Literature 6] Nakamura H, Moriyama Y, Makiyama T, Emori S, Yamashita H, Yamazaki R, Murayama T. Lactosylceramideinteracts with and activates cytosolic phospholipase A2α. J Biol Chem. 2013 Aug. 9; 288 (32): 23264-72.

[Non-patent Literature 7] Pannu R, Singh A K, Singh I. A novel role of lactosylceramide in the regulation of tumor necrosis factor alphamediated proliferation of rat primary astrocytes. Implications for astrogliosis following neurotrauma. J Biol Chem. 2005 Apr. 8; 280 (14): 13742-51.

[Non-patent Literature 8] Kolmakova A, Chatterjee S. Platelet derived growth factor recruits lactosylceramide to induce cell proliferation in UDP Gal:GlcCer: beta1→4Galactosyltransferase (GalT-V) mutant Chinese hamster ovary cells. Glycoconj J. 2005 November; 22 (7-9): 401-7.

[Non-patent Literature 9] Mayo L, Trauger S A, Blain M, Nadeau M, Patel B, Alvarez J I, Mascanfroni I D, Yeste A, Kivisakk P, Kallas K, Ellezam B, Bakshi R, Prat A, Antel J P, Weiner H L, Quintana F J. Regulation of astrocyte activation by glycolipids drives chronic CNS inflammation. Nat Med. 2014 October; 20 (10): 1147-56.

[Non-patent Literature 10] Bodas M, Min T, Vij N. Lactosylceramide-accumulation in lipid-rafts mediate aberrant-autophagy, inflammation and apoptosis in cigarette smoke induced emphysema. Apoptosis. 2015 May; 20 (5): 725-39.

SUMMARY

An object of the present invention is to provide a therapeutic agent for fibrosis that inhibits the nuclear translocation of phosphorylated Smad to treat and prevent fibrosis.

Any discussion of problems and solutions involved in the related art has been included in this disclosure solely for the purposes of providing a context for the present invention, and should not be taken as an admission that any or all of the discussion were known at the time the invention was made.

1. A therapeutic agent for fibrosis characterized in that its active ingredient is constituted by a glucosylceramide synthase inhibitor or lactosylceramide synthase inhibitor, or both.

2. A therapeutic agent for fibrosis according to 1, characterized in that the glucosylceramide synthase inhibitor is constituted by one or more substances selected from 1-phenyl-2-hexadecanoyl amino-3-morpholino-1-propanol (PPMP), 1-phenyl-2-decanoyl amino-3-morpholino-1-propanol (PDMP), N-butyl deoxynojirimycin (Miglustat, NB-DNJ), N-butyl deoxygalactonojirimycin (NB-DGJ), deoxynojirimycin (DNJ), and N-[(1R,2R)-1-(2,3-dihydrobenzo[b][1,4]dioxine-6-yl)-1-hydroxy-3-(pyrrolidine-1-yl) propane-2-yl]octane amide hemi-(2R,3R)-tartrate (Eliglustat tartrate).

3. A therapeutic agent for fibrosis according to 1, characterized in that the lactosylceramide synthase inhibitor is constituted by one or more substances selected from N-dodecyl deoxynojirimycin, nojirimycin sulfite adduct, nojirimycin sulfite adduct hydrophobic derivative, and salts thereof.

4. A therapeutic agent for fibrosis according to any one of 1 to 3, characterized in that it is an agent to treat or prevent idiopathic pulmonary fibrosis.

5. An inhibitor of nuclear translocation of phosphorylated Smad, whose active ingredient is constituted by a glucosylceramide synthase inhibitor or lactosylceramide synthase inhibitor, or both.

The inventors of the present invention found a TGFβ1 signal control mechanism for controlling the nuclear translocation of phosphorylated Smad that transmits the αSMA and collagen synthesizing signals from TGFβ1. The therapeutic agent for fibrosis proposed by the present invention is based on this new mechanism, and inhibits the nuclear translocation of phosphorylated Smad.

The therapeutic agent for fibrosis proposed by the present invention uses a glucosylceramide synthase inhibitor or lactosylceramide synthase inhibitor as its active ingredient and inhibits the nuclear translocation of phosphorylated Smad, to suppress the synthesis of αSMA and collagen that cause fibrosis. The therapeutic agent for fibrosis proposed by the present invention suppresses the process of expression of proteins relating to the fibrosing of tissue, and can be used for the treatment and prevention of fibrosis in various tissues including those of the lung, kidney, liver, heart, skin, bone marrow, pancreas, eye, etc.; in particular, it is expected to be applied to agents that treat and prevent idiopathic pulmonary fibrosis.

N-butyl deoxynojirimycin (Miglustat, NB-DNJ), which is a glucosylceramide synthase inhibitor, has been approved as an oral treatment drug for Gaucher's disease and Niemann-Pick disease type C. Since drug agents that are already used as treatment drugs for other diseases generally present little risk of side effects and are very safe, there is hope that an therapeutic agent for fibrosis whose active ingredient is miglustat can be applied to clinical research.

For purposes of summarizing aspects of the invention and the advantages achieved over the related art, certain objects and advantages of the invention are described in this disclosure. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description which follows.

BRIEF DESCRIPTION OF THE DRAWINGS

These and other features of this invention will now be described with reference to the drawings of preferred embodiments which are intended to illustrate and not to limit the invention. The drawings are greatly simplified for illustrative purposes and are not necessarily to scale.

FIGS. 6A and 6B are confocal laser microscope images of HFL1 cells (Smad2 in FIG. 6A, Smad3 in FIG. 6(B)) in Experiment 3.

DETAILED DESCRIPTION OF EMBODIMENTS

The inventors of the present invention found a new TGFβ1 signal control mechanism not heretofore known, which is that TGFβ1 induces increased synthesis of lactosylceramide, and this lactosylceramide positively controls the nuclear translocation of phosphorylated Smad via protein kinase Cδ (PKCδ)/Rho binding kinase (ROCK) signals.

Figure 1:
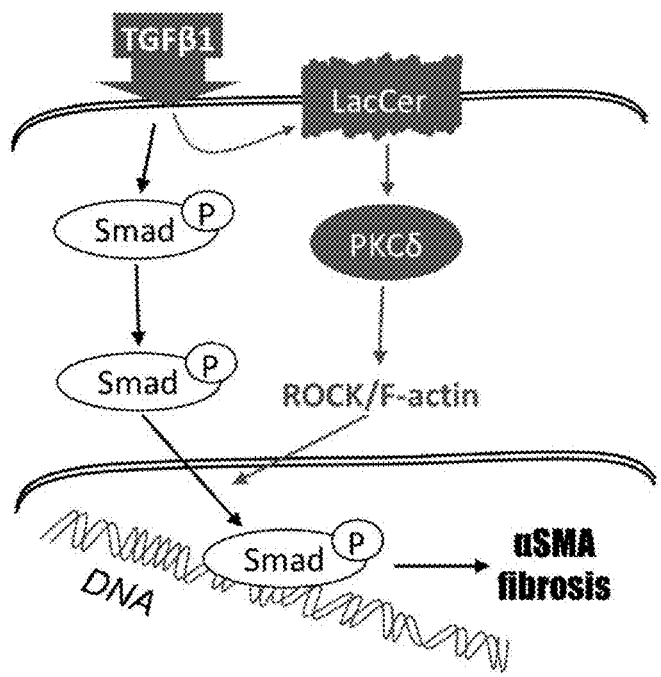
FIG. 1 is a schematic drawing of a pathway for controlling the nuclear translocation of phosphorylated Smad by way of increasing the synthesis of lactosylceramide based on TGFβ1 stimulation.

FIG. 1 shows a schematic drawing of the pathway of this mechanism.

That TGFβ1 induces increased synthesis of lactosylceramide, and that lactosylceramide activates PKCδ/ROCK signals to control the nuclear translocation of phosphorylated Smad, are new findings by the inventors of the present invention that were not heretofore known.

As is evident from this pathway, lactosylceramide synthase inhibitors, PKCδ inhibitors, and ROCK inhibitors inhibit the nuclear translocation of phosphorylated Smad. In addition, glucosylceramide synthase inhibitors that inhibit synthases for glucosylceramide, which is a precursor to lactosylceramide, also inhibit the nuclear translocation of phosphorylated Smad. Accordingly, lactosylceramide synthase inhibitors, glucosylceramide synthase inhibitors, PKCδ inhibitors, and ROCK inhibitors can also be used as inhibitors of nuclear translocation of phosphorylated Smad.

The therapeutic agent for fibrosis proposed by the present invention whose active ingredient is constituted by a glucosylceramide synthase inhibitor or lactosylceramide synthase inhibitor, or both, inhibits the nuclear translocation of phosphorylated Smad in the aforementioned pathway and thereby suppresses the transcription and translation of target genes that contain αSMA and other proteins relating to fibrosing. Since the mechanism of how they are synthesized and expressed due to phosphorylated Smad is the same with all proteins relating to fibrosing, the therapeutic agent for fibrosis proposed by the present invention can be used as an agent to treat or prevent fibrosis in various tissues including those of the lung, kidney, liver, heart, skin, bone marrow, pancreas, eye, etc.

The glucosylceramide synthase inhibitor used as the therapeutic agent for fibrosis proposed by the present invention is not limited in any way, and any one or more substances selected from 1-phenyl-2-hexadecanoyl amino-3-morpholino-1-propanol (PPMP), 1-phenyl-2-decanoyl amino-3-morpholino-1-propanol (PDMP) having the same basic skeleton as PPMP, N-butyl deoxynojirimycin (Miglustat, NB-DNJ), N-butyl deoxygalactonojirimycin (NB-DGJ), deoxynojirimycin (DNJ), N-[(1R,2R)-1-(2,3-dihydrobenzo [b][1,4] dioxine-6-yl)-1-hydroxy-3-(pyrrolidine-1-yl) propane-2-yl] octane amide hemi-(2R,3R)-tartrate (Eliglustat tartrate), etc., may be used, for example.

The lactosylceramide synthase inhibitor used as the therapeutic agent for fibrosis proposed by the present invention is not limited in any way, and any one or more substances selected from N-dodecyl deoxynojirimycin, nojirimycin sulfite adduct, nojirimycin sulfite adduct hydrophobic derivative, salts thereof, etc., may be used, for example.

It should be noted that PPMP and NB-DNJ each act as a glucosylceramide synthase inhibitor and also as a lactosylceramide synthase inhibitor.

For the therapeutic agent for fibrosis proposed by the present invention, an inhibitor of nuclear translocation of phosphorylated Smad may be used directly on its own; preferably, however, pharmacologically permitted drug additives are used to deliver such inhibitor as a drug composition. For the pharmacologically permitted formulation additives, as described in this Specification, sizing agents, stabilizers, preservatives, buffer agents, taste-masking agents, suspension agents, emulsifiers, flavoring agents, solubilizing agents, coloring agents, thickening agents, etc., may be used.

The therapeutic agent for fibrosis proposed by the present invention may be administered orally, non-orally, or by both means. Drug compositions suitable for oral administration include pills, granules, capsules, dispersions, solutions, suspensions, syrups, etc., for example, while drug compositions suitable for non-oral administration include inhalants, injections, drops, suppositories, percutaneous aspirations, etc., for example; however, the forms of drugs that can be used under the present invention are not limited to the foregoing.

The therapeutic agent for fibrosis proposed by the present invention may be administered to mammals including humans. The dosage of the agent proposed by the present invention is determined according to the age, sex, weight, condition, and administration pathway of the patient, and other conditions. The dosage of the therapeutic agent for fibrosis proposed by the present invention, for adult per day, is normally in a range of 0.001 mg/kg or more but no more than 2000 mg/kg, or preferably 0.01 mg/kg or more but no more than 500 mg/kg, or more preferably 0.1 mg/kg or more but no more than 200 mg/kg, or most preferably 1 mg/kg or more but no more than 100 mg/kg. The therapeutic agent for fibrosis proposed by the present invention may be administered daily, or at an interval of one to four days.

Example

Method of Experimentation

Cell Culturing

Human pulmonary fibroblast (HFL1) (ATCC CCL-153) cells were cultured under the conditions of 95% air-5% $CO_2$ and 37° C., using a Dulbecco's Modified Eagle Medium (DMEM) containing 10% fetal bovine serum (FBS), 100 μg/mL streptomycin, and 66.7 μg/mL penicillin.

Western Blot

HFL1 cells were inoculated onto a six-well plate by $1.0 \times 10^5$ cells/well, and then cultured in 2.0 mL of DMEM containing 10% FBS, to achieve 70% confluence. The cells were washed using Hanks' balanced salt solution (HBSS) containing 0.1% bovine serum albumin (BSA) (4.2 mM $NaHCO_3$, 137 mM NaCl, 5.36 mM KCl, 0.4 mM $MgSO_4 \cdot 7H_2O$, 0.34 mM $Na_2HPO_4 \cdot 12H_2O$, 5.55 mM glucose, 0.44 mM $KH_2PO_4$, 0.72 mM $CaCl_2 \cdot H_2O$, pH=7.4), and then cultured in a DMEM containing 0.1% BSA for 48 hours without serum.

Thereafter, the medium was replaced by a DMEM containing 0.1% BSA, and stimulation was given for a specified period using each reagent (each inhibitor was applied 30 minutes before the stimulant), after which the cells were collected on ice using 100 μL of RIPA buffer (150 mM NaCl, 50 mM Tris-HCl, 5 mM EDTA, 5 mM NaF, 10 mM sodium pyrophosphate dibasic, 1% Nonidet P-40, 0.1% sodium dodecyl sulfate, 0.5% sodium deoxycholate, pH 8.0) containing 10 μg/mL aprotinin, 10 μg/mL leupeptin, and phenyl methyl sulfonyl fluoride (PMSF) as a protease inhibitor.

The cells were crushed according to the vortex method, centrifuged under the conditions of 15000 rpm and 4° C. for 30 minutes, and the supernatant was taken as a sample. Quantitative determination of protein was performed according to the Bradford method, and a specified amount of protein was separated by SDS-polyacrylic amide gel electrophoresis. The protein was transferred onto a polyvinylidene difluoride (PVDF) film, blocked for 1 hour at room temperature, with a primary antibody applied overnight at 4° C., and a secondary antibody applied for 1 hour at room temperature. The conditions for each antibody are shown in Table 1.

Thereafter, the PVDF film was soaked in an ECL solution and fluorometric detection was performed using an image capture/analysis system (ChemiDocMP System manufactured by Bio-Rad). The detected bands were converted to numerical values using image processing software (ImageJ).

TABLE 1

| Antibody | Blocking | 1st antibody | 2nd antibody |
| --- | --- | --- | --- |
| P-Smad2 | 1%SkimMilk/TBS-T | 1%SkimMilk/TBS-T,x1000 | 1%SkimMilk/TBS-T,x2000(rabbit) |
| Smad2 | 5%BSA/TBS-T | 3%BSA/TBS-T,x2000 | 3%BSA/TBS-T,x2000(rabbit) |
| P-Smad3 | 1%SkimMilk/TBS-T | 1%SkimMilk/TBS,x1000 | 1%SkimMilk/TBS-T,x2000(rabbit) |
| Smad3 | 5%BSA/TBS-T | 3%BSA/TBS-T,x1000 | 3%BSA/TBS-T,x2000(rabbit) |
| α-SMA | 5%BSA/TBS-T | 3%BSA/TBS-T,x2000 | 3%BSA/TBS-T,x4000(mouse) |
| β-tubulin | 5%BSA/TBS-T | 3%BSA/TBS-T,x2000 | 3%BSA/TBS-T,x4000(mouse) |
| GCS | 3%BSA/TBS-T | 3%BSA/TBS-T.x500 | 3%BSA/TBS-T,x2000(goat) |

Immunofluorescent Staining Test

HFL1 cells were inoculated onto a 3.5-cm glass-bottom dish by $1.0 \times 10^4$ cells/dish, and then cultured in 2.0 mL of DMEM containing 10% FBS, to achieve 70% confluence. The cells were washed in HBSS containing 0.1% BSA, and then cultured in DMEM containing 0.1% BSA for 48 hours without serum.

Thereafter, the medium was replaced by a DMEM containing 0.1% BSA, and stimulation was given for a specified period using each reagent (each inhibitor was applied 30 minutes before the stimulant), after which each sample was fixed with 4% paraformaldehyde (PFA) at 4° C. for 15 minutes. Thereafter, as deemed appropriate, the sample was permeabilized (0.3% saponin, room temperature, 1 hour) and blocked (3% BSA, room temperature, 1 hour), with a primary antibody applied overnight at 4° C., and a secondary antibody applied for 1 hour at room temperature. For immunostaining of Smad and phosphorylated Smad, ribonuclease A (RNase, Worthington Biochemical) (200 μg/mL, room temperature, 30 minutes) and propidium iodide (PI, Cayman Chemical) (20 μg/mL, room temperature, 30 minutes) were applied to stain the nucleus, and the stained images were observed using a confocal microscope (FV500 manufactured by Olympus).

Lactosylceramide Synthesis Activation Test

The experiment was conducted by referring to Chatterjee S, Pandey A. The Yin and Yang of lactosylceramide metabolism: implications in cell function. Biochim Biophys Acta. 2008 March; 1780 (3); 370-82.

HFL1 cells were inoculated onto a 10-cm dish by $5 \times 10^5$ cells/dish, and then cultured in 8 mL of DMEM containing 10% FBS, to achieve 70% confluence. The cells were washed in HBSS containing 0.1% BSA, and then cultured in DMEM containing 0.1% BSA for 48 hours without serum. Thereafter, the medium was replaced by a DMEM containing 0.1% BSA, and stimulation was given for a specified period using each reagent (each inhibitor was applied 30 minutes before the stimulant), after which the cells were collected using 1 mL of phosphoric acid buffer saline solution per dish and then centrifuged (4° C., 3000 rpm, 10 minutes), and the obtained pellets were suspended in 100 μL of reaction buffer (1 mM $MgCl_2$, 1 mM $MnCl_2$, 20 mM sodium cacodylate trihydrate, 0.0067% Triton X-100, 0.0125% NP-40) per tube, and the cells were crushed using supersonic waves.

The sample was put through quantitative determination of protein, and then 300 μM of galactosylceramide, 100 μM of uridine diphosphate galactose (UDP-Gal, containing 7.5× $10^5$ dpm of [$^3$H] UDP-Gal), and reaction buffer, were added to 50 μL of sample, to a final volume of 100 μL/tube. This reaction sample was incubated for 2 hours at 37° C., and finally 50 mM of KCl and 25 mM of EDTA were added to stop the reaction. Thereafter, lipids were extracted from the sample according to the Bligh-Dyer method, and all lipids were expanded using TLC (chloroform:methanol:water=100:42:6). The separated lipids were stained using iodine gas, silica gel at the same position as the lactosylceramide target was scraped off, and its radiation activity was measured using a liquid scintillation counter (Aloka LSC-5100 manufactured by Hitachi-Aloka Medical), and then the amount of synthesized lactosylceramide was calculated. It should be noted that, for the background sample (control), a sample with zero incubation time was used.

Data Processing

The average±standard deviation was obtained from at least three separate experiments. Significant difference between two groups was tested using the Student's paired t-test, and the difference was judged significant when the risk rate was less than 5%.

Figure 2:
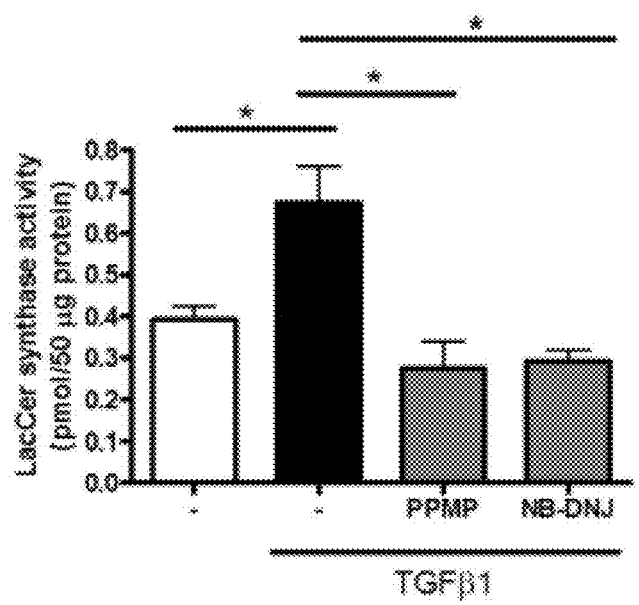
FIG. 2 is a graph showing the result of Experiment 1 which is a lactosylceramide synthesis activation test.

Experiment 1: Examination of Effects of TGFβ1 on Lactosylceramide Synthesis Activity Whether or not TGFβ1 treatment would increase the synthesis of lactosylceramide was examined in vitro. The results are shown in FIG. 2.

When the HFL1 cells were treated with TGFβ1 (10 ng/mL), the activity of the lactosylceramide synthase increased after 30 minutes of stimulation. Also, application of the glucosylceramide synthase inhibitors PPMP (3 μM) and NB-DNJ (100 μM) 30 minutes before the TGFβ1 stimulation suppressed the activity of the lactosylceramide synthase significantly.

It was confirmed that TGFβ1 increases the lactosylceramide synthesis activity, and that the glucosylceramide synthase inhibitors suppress rise in this activity.

Experiment 2: Examination of Effects of Lactosylceramide on αSMA Expression

How an increase in lactosylceramide synthesis activity due to TGFβ1 affects the fibrosing of tissues was examined based on the expression level of αSMA, which is a fibrosing marker protein. The results are shown in FIGS. 3A to 3C.

When the HFL1 cells were treated with TGFβ1 (10 ng/mL) for 24 hours, the αSMA expression level increased significantly.

Application of the glucosylceramide synthase inhibitors PPMP (3 μM) and NB-DNJ (100 μM) 30 minutes before the TGFβ1 stimulation suppressed increase in the αSMA expression level. Also, combined use of lactosylceramide (10 μM) and PPMP or NB-DNJ led to a recovery of the αSMA expression level suppression action (FIGS. 3A and B). When PPMP and lactosylceramide were used together, the αSMA expression level recovered to approx. 95% of the level achieved when TGFβ1 alone was applied. It should be noted that combined use of PPMP with glucosylceramide, instead of lactosylceramide, also caused the αSMA expression level to recover to approx. 80% (FIG. 4).

Figures 3A, 3B, 3C:
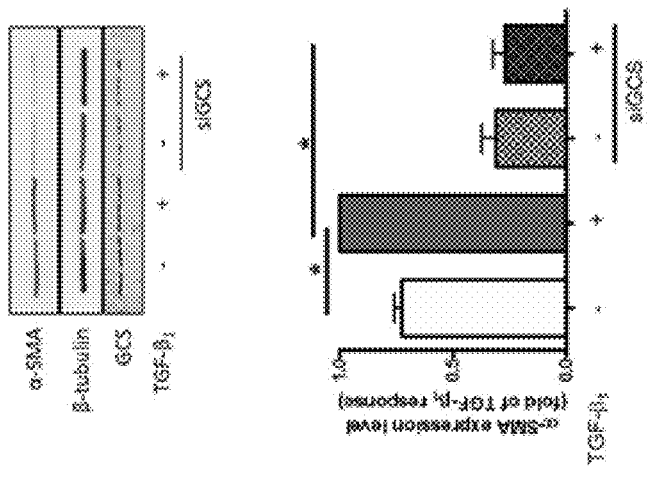
FIGS. 3A, 3B, and 3C are graphs showing the αSMA expression levels in Experiment 2 in relation to: PPMP (FIG. 3A), NB-DNJ (FIG. 3B), and Knock-out of glucosylceramide synthase (FIG. 3C).
Figure 4:
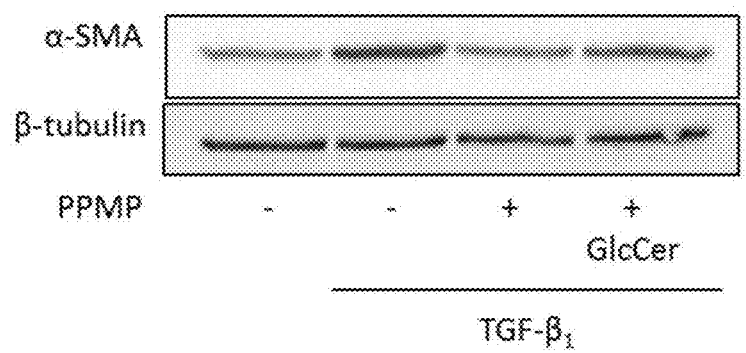
FIG. 4 is western blot images showing the results of expression of human pulmonary fibroblast (HFL1) cell αSMA and β-tubulin in Experiment 2.

Additionally, when the glucosylceramide synthase (GCS), which is a precursor to lactosylceramide, was knocked down, the TGFβ1 stimulation-induced increase in the αSMA expression level was suppressed significantly (FIG. 3C).

The aforementioned results confirm that TGFβ1 presents a signal pathway by way of increase in lactosylceramide synthesis, and that this signal pathway promotes the fibrosing of tissues (expression of αSMA). It was also confirmed that this signal transmission is accompanied by an increase in the amount of lactosylceramide in the cell.

Experiment 3: Examination of Effects of Lactosylceramide on Smad Signals

Smad2/3 are transcription factors and known to promote the transcription activity of molecules relating to fibrosing, by undergoing direct phosphorylation due to the activated TGF-β receptor and then nuclear translocation (Non-patent Literature 4).

How lactosylceramide affects Smad signals was examined. The results are shown in FIGS. 5A to 6B.

Figure 5A:
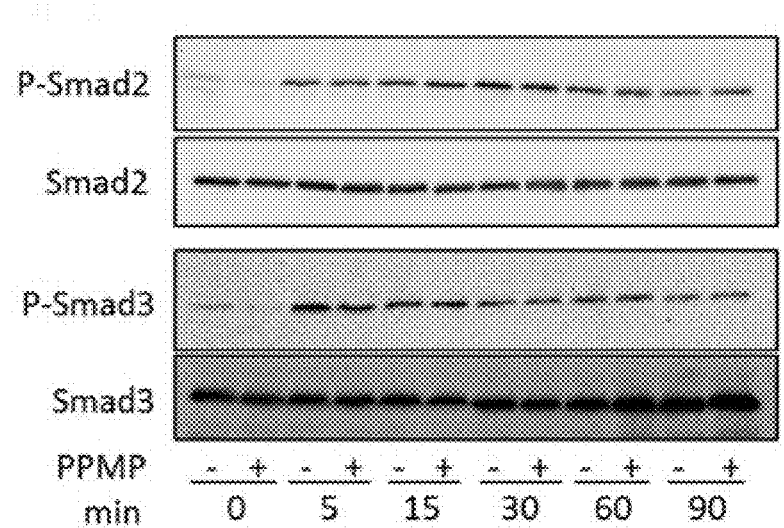
FIGS. 5A and 5B are western blot images showing the results of expression of HFL1 Smad2/3 and phosphorylated Smad2/3 (FIG. 5A in relation to PPMP), and expression of phosphorylated Smad2 (FIG. 5B in relation to Lactosylceramide) in Experiment 3.
Figure 5B:
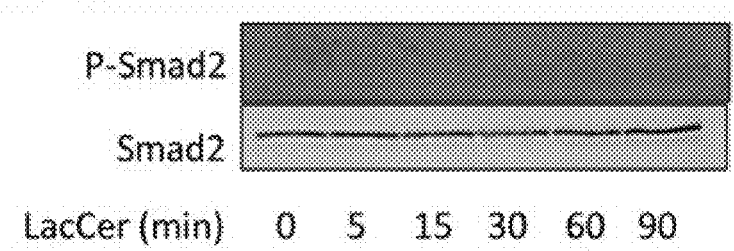

When the phosphorylation levels of Smad2/3 were examined, application of PPMP (3 μM) 30 minutes before the TGFβ1 (10 ng/mL) treatment did not change the phosphorylation levels of Smad2/3 over time (FIG. 5A). Also, application of lactosylceramide (10 μM) alone to the cells did not cause phosphorylation of Smad2 (FIG. 5 B).

When localization of Smad2/3 was observed, on the other hand, Smad2/3 accumulated in the nucleus in 3 hours after the single stimulation of TGFβ1 (10 ng/mL). However, pretreatment with PPMP (3 μM) or NB-DNJ (100 μM) suppressed the accumulation of Smad2 in the nucleus. Furthermore, combined use of lactosylceramide (10 μM) and PPMP led to a recovery of the suppression action due to PPMP, and Smad2 accumulated in the nucleus (FIG. 6A). Also, similar operations and effects were demonstrated with respect to Smad3 (FIG. 6B).

The above results confirm that lactosylceramide does not affect phosphorylation of Smad and that it positively controls the nuclear localization of Smad2/3 due to TGFβ1.

Experiment 4: Examination of Effects of Lactosylceramide on PKCδ

Which intracellular signals are involved in the control of the localization of Smad by lactosylceramide, was examined.

Activation of PKCα/ε is a known intracellular signal triggered by lactosylceramide on the cellular membrane (Chatterjee S, Pandey A. The Yin and Yang of lactosylceramide metabolism: implications in cell function. Biochim Biophys Acta. 2008 March; 1780 (3): 370-82). PKC is an enzyme that phosphorylates proteins, manifesting in the tissues throughout our body and involved in various bioactivities such as gene expression, cell growth, and cell death. PKCs are classified into three types, including "conventional PKC" that requires diasylglycerol and $Ca^{2+}$ for activation, "novel PKC" that requires only diasylglycerol for activation, and "atypical PKC" that is activated through other mechanisms. Known PKCs of mammals include 10 types of isoforms including α, βI, βII, γ, δ, and the like.

Figure 7A:
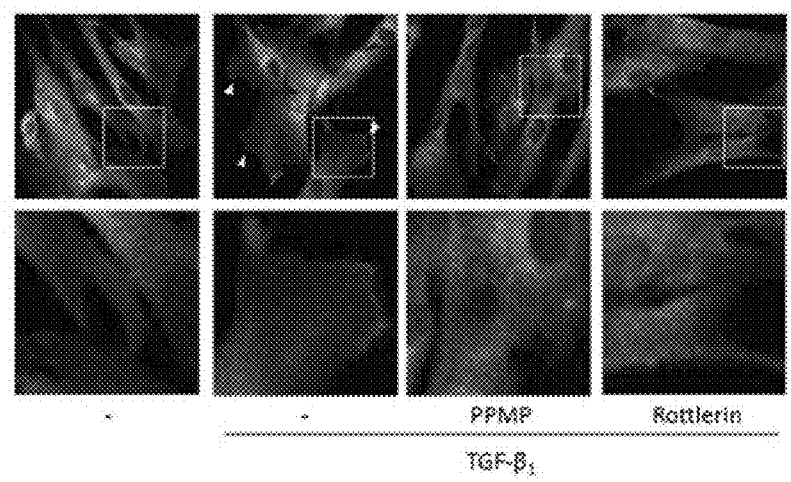
FIGS. 7A and 7B are confocal laser microscope images of HFL1 cells in Experiment 4 in relation to: PPMP and Rottlerin (FIG. 7A), and Lactosylceramide (FIG. 7B).
Figure 7B:
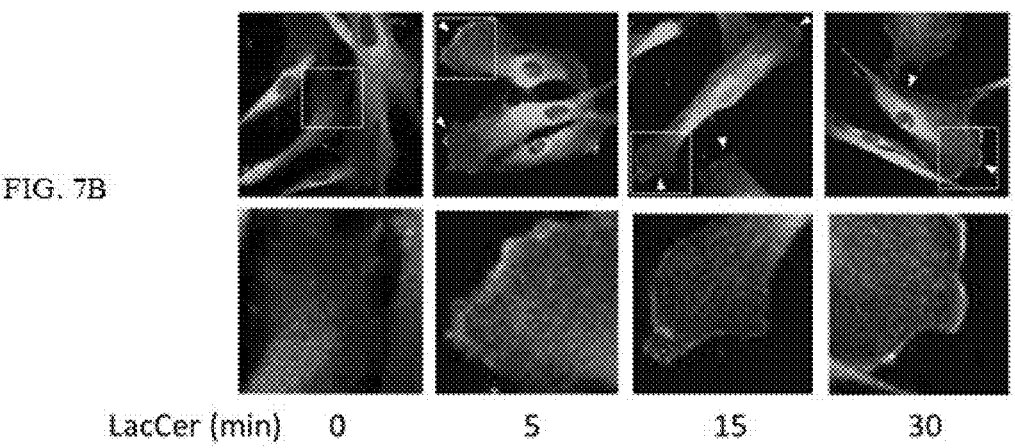

The inventors of the present invention built a hypothesis that lactosylceramide, through activation of PKCδ, controls the localization of Smad2/3 due to TGFβ1, and examined this hypothesis. The results are shown in FIGS. 7A and 7B. In each of FIGS. 7A and 7B, the photographs at the bottom show enlarged views of the areas inside the white squares in the photographs at the top.

In general, activation of PKC is observed in the form of its translocation into the cellular membrane; accordingly, involvement of lactosylceramide was examined using the translocation of PKCδ into the cellular membrane as an indicator.

Two hours after the cells were treated with TGFβ1 (10 ng/mL), translocation of PKCδ into the cellular membrane occurred. However, translocation of PKCδ into the cellular membrane was suppressed when PPMP (3 μM), or Rottlerin (1 μM) which is a PKCδ inhibitor, was applied beforehand (FIG. 7A). In addition, translocation of PKCδ into the cellular membrane was observed five minutes after the stimulation by lactosylceramide (10 μM) alone, and the localization of PKCδ on the cellular membrane was sustained for at least 30 minutes (FIG. 7B).

The above results confirm that TGFβ1 activates PKCδ, and that lactosylceramide mediates this activation.

Experiment 5: Examination of Effects of PKCδ on TGFβ1/Smad Signals

Involvement of PKCδ in the TGFβ1/Smad signals was examined. The results are shown in FIGS. 8A to 11B.

First, involvement of PKCδ in the expression of αSMA was examined. It is known that overnight treatment with PMA (phorbol myristate acetate) causes down-regulation of conventional PKC and novel PKC.

Figure 8A:
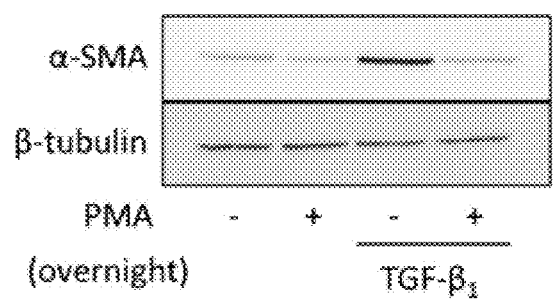
FIGS. 8A and 8B are western blot images showing the results of expression of HFL1 αSMA and β-tubulin in Experiment 5 (FIG. 8A), and a graph showing the αSMA expression levels (FIG. 8B).
Figure 8B:
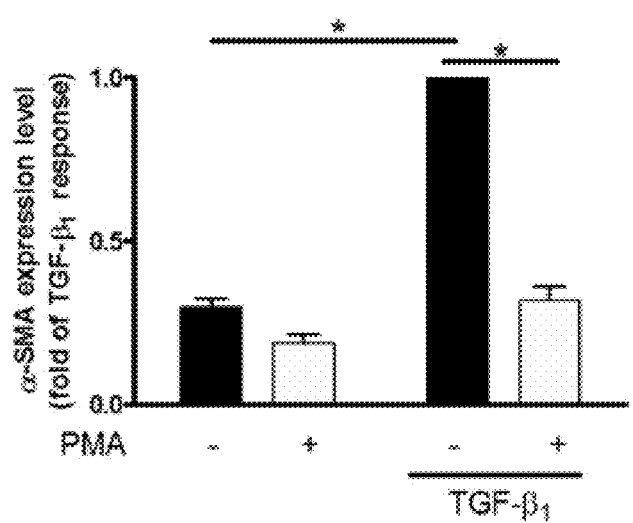

Treatment with PMA (100 nM) suppressed the increase in the αSMA expression level due to TGFβ1 (10 ng/mL) (FIGS. 8A and 8B).

Figure 9A:
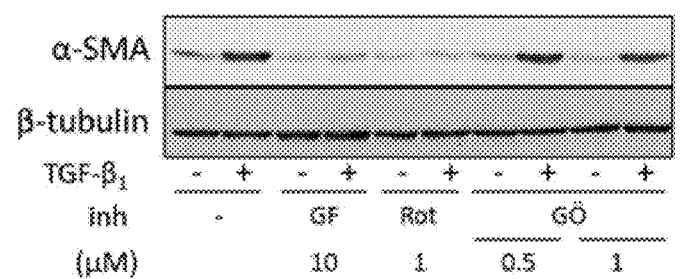
FIGS. 9A and 9B are western blot images showing the results of expression of HFL1 αSMA and β-tubulin when each PKC inhibitor was applied (FIG. 9A), and a graph showing the αSMA expression levels (FIG. 9B) in Experiment 5.
Figure 9B:
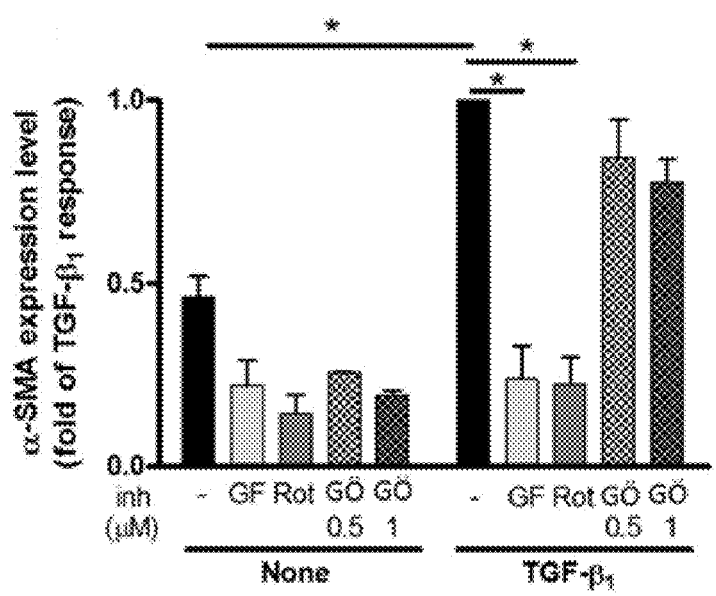

The increase in the αSMA expression level due to TGFβ1 was also suppressed significantly when GF109203X (10 μM) that inhibits PKCα/β/δ/γ, or Rottlerin (1 μM) which is a PKCδ inhibitor, was applied 30 minutes before the TGFβ1 (10 ng/mL) stimulation. On the other hand, treatment of the cells with G06976 ("O" is umlaut-O) (0.5 μM, 1.0 μM) that does not inhibit PKCδ but inhibits PKCα/β, did not suppress the increase in the αSMA expression level (FIGS. 9A and 9B).

Figure 10:
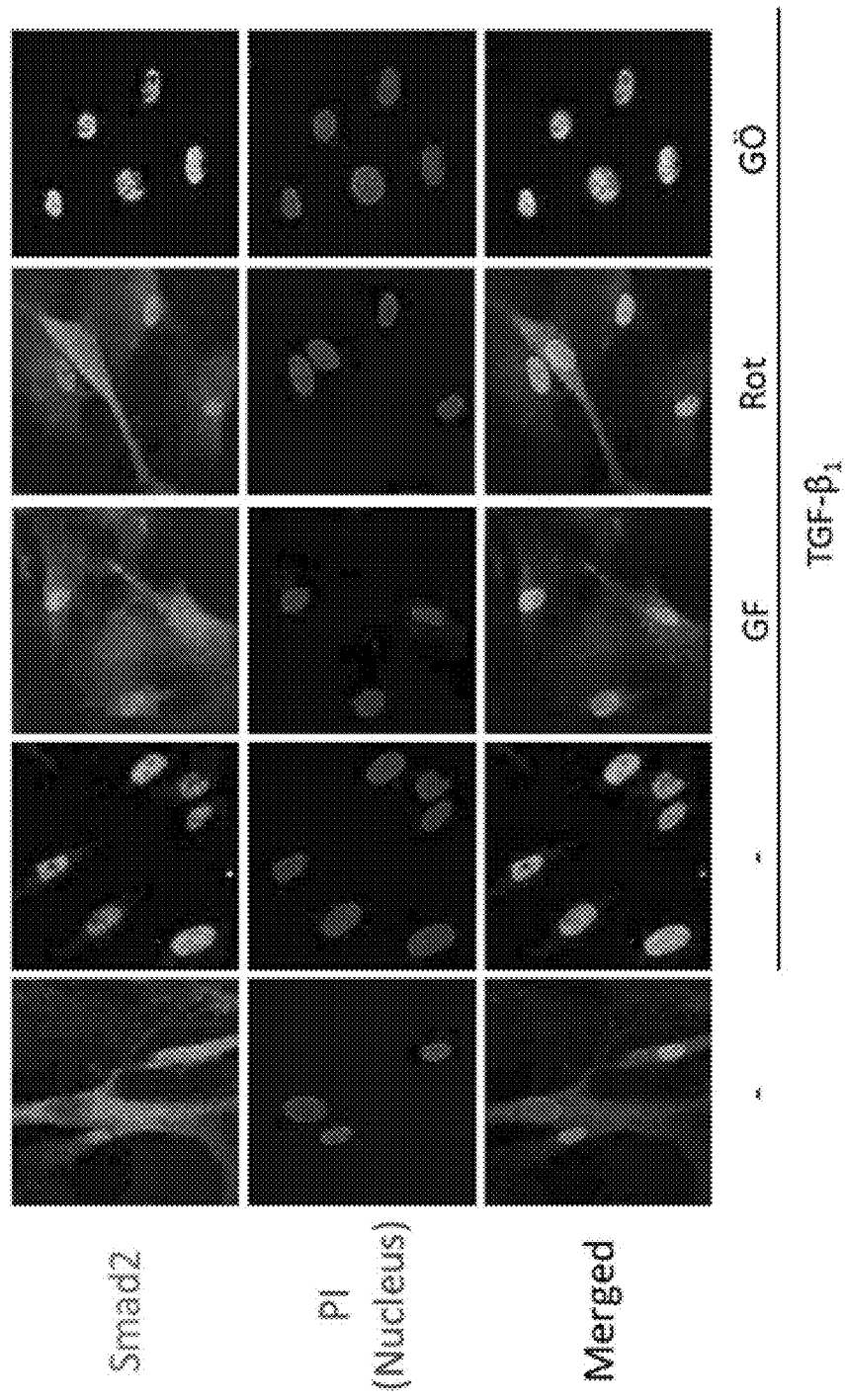
FIG. 10 is confocal laser microscope images of HFL1 cells in Experiment 5.

Next, when the effects of PKCδ on Smad2 were examined, the nuclear localization of Smad2 due to TGFβ1 (10 ng/mL) was suppressed significantly when GF109203X (10 μM) or Rottlerin (1 μM) was applied, but it did not change when G06976 ("O" is umlaut-O) (1 μM) was applied (FIG. 10).

Figure 11A:
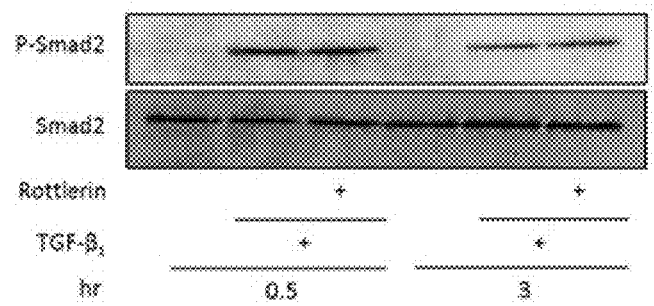
FIGS. 11A and 11B are western blot images showing the results of expression of HFL1 Smad2 and phosphorylated Smad2 in Experiment 5 in relation to: Rottlerin (FIG. 11A), and GF109203X (FIG. 11B).
Figure 11B:
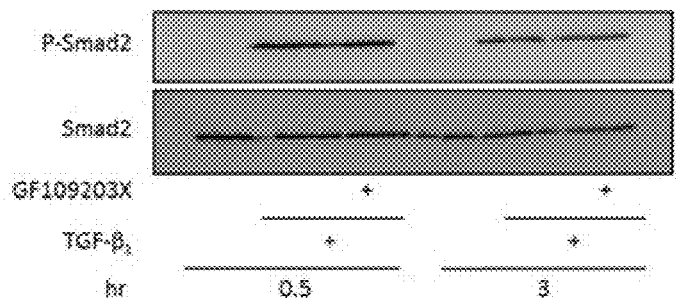

Also, with respect to the phosphorylation level of Smad2 due to the TGFβ1 (10 ng/mL) treatment, no change was observed when GF109203X (10 μM) or Rottlerin (1 μM) was applied (FIGS. 11A and 11B).

The above results confirm that PKCδ mediates the control of nuclear localization of Smad by lactosylceramide. It was also confirmed that PKCδ is not involved in the phosphorylation of Smad2.

Experiment 6: Examination of Effects of ROCK Pathway on TGFβ1/Smad Signals

As for the mechanism of how PKCδ controls Smad, it has been reported that PKCδ negatively controls the Smad phosphatase via a ROCK pathway (Lin X, Duan X, Liang Y Y, Su Y, Wrighton K H, Long J, Hu M, Davis C M, Wang J, Brunicardi F C, Shi Y, Chen Y G, Meng A, Feng X H. PPM1A functions as a Smad phosphatase to terminate TGFbeta signaling. Cell. 2006 Jun. 2; 125 (5): 915-28).

In this study, it was assumed that a similar pathway would be present, and the αSMA expression level was examined using Y27632 which is a ROCK inhibitor, and Cytochalasin B that inhibits actin polymerization downstream of ROCK. The results are shown in FIGS. 12A to 13B.

Figure 12A:
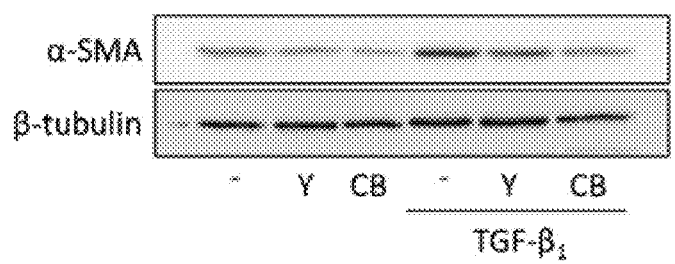
FIGS. 12A and 12B are western blot images showing the results of expression of HFL1 αSMA and β-tubulin (FIG. 12A), and a graph showing the αSMA expression levels (FIG. 12B) in Experiment 6.
Figure 12B:
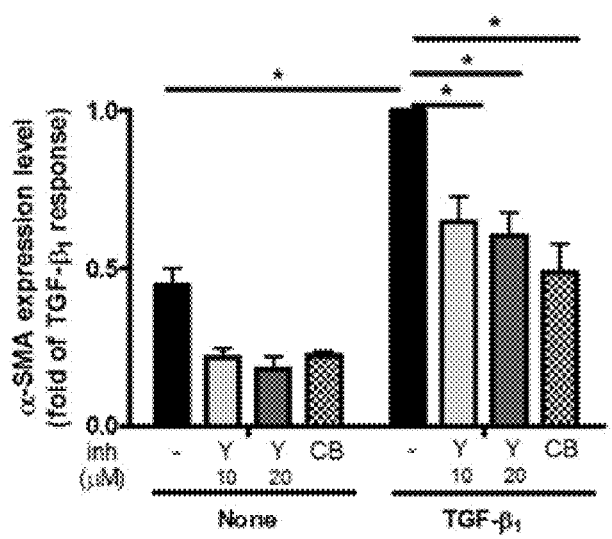

The increase in the αSMA expression level due to TGFβ1 (10 ng/mL) was suppressed by Y27632 (10 μM, 20 μM: the western blot image reflects 10 μM) and Cytochalasin B (2 μM) (FIGS. 12A and 12B).

Figure 13A:
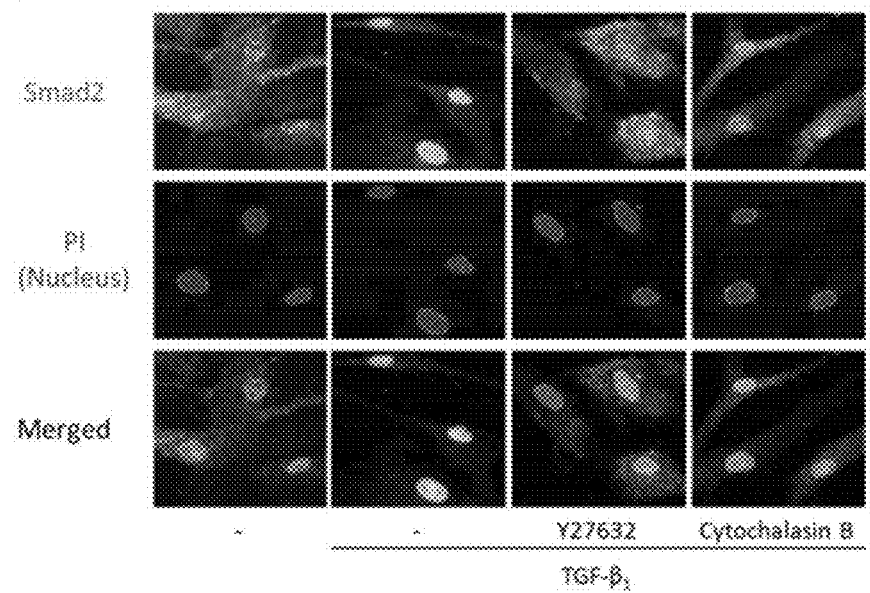
FIGS. 13A and 13B are confocal laser microscope images of HFL1 cells in Experiment 6 (FIG. 13A), and western blot images showing the results of expression of HFL1 Smad2 and phosphorylated Smad2 in Experiment 6 (FIG. 13B).
Figure 13B:
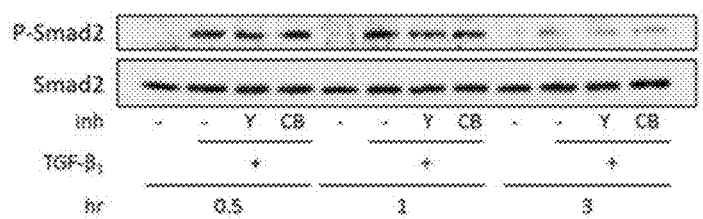

Also, when the effects of Y27632 (20 μM) and Cytochalasin B (2 μM) on Smad2 were examined, the nuclear translocation of Smad2 due to TGFβ1 (10 ng/mL) was suppressed, but the phosphorylation level did not change (FIGS. 13A and 13B).

The above confirms that ROCK mediates the nuclear localization of Smad. It also confirms that ROCK is not involved in the phosphorylation of Smad2.

Experiment 7: Establishment of Patient's Pulmonary Fibroblast Cells

Patient's Pulmonary Fibroblast Cells

Post-operative lung tissues were obtained from a 19-year-old male lung transplant patient who was suffering from a serious case of pleuroparenchymal fibroelastosis.

The lung tissues were shredded, rinsed with phosphate-buffered saline (PBS), and then incubated at 37° C. for 15 minutes under gentle shaking, using 1 mg/ml collagenase type I (Worthington, Lakewood, N.J., USA), 0.5 mg/ml disperse (Life Technologies), 2 U/ml DNase (QIAGEN, Valencia, Calif., USA), 0.1 mg/ml streptomycin, and 100 U/ml penicillin.

The tissues were washed twice in DMEM, and then transferred into an 80-cm$^2$ culture flask and cultured at 37° C. in 5% $CO_2$.

Cell growth was monitored every week, with the culture medium changed every four days. Once the flask reached confluent cultures, the cells were collected as cells at passage 0, and the cells obtained at passage 3 were used in the experiment as the patient's pulmonary fibroblast cells.

Cell Culture

Patient's pulmonary fibroblast cells were cultured under the conditions of 95% air-5% $CO_2$ and 37° C., using a Dulbecco's Modified Eagle Medium (DMEM) containing 10% fetal bovine serum (FBS), 100 μg/mL streptomycin, and 66.7 μg/mL penicillin.

Western Blot

The patient's pulmonary fibroblast cells were inoculated onto a six-well plate by $1.0 \times 10^5$ cells/well, and then cultured in 2.0 mL of DMEM containing 10% FBS to achieve 90 to 95% confluence. Thereafter, PPMP (0.5 μM, 1.0 μM) or NB-DNJ (100 μM, 200 μM) was added, and the cells were cultured for 48 hours and then collected on ice using 100 μL of RIPA buffer (150 mM NaCl, 50 mM Tris-HCl, 5 mM EDTA, 5 mM NaF, 10 mM sodium pyrophosphate dibasic, 1% Nonidet P-40, 0.1% sodium dodecyl sulfate, 0.5% sodium deoxycholate, pH 8.0) containing 10 μg/mL aprotinin, 10 μg/mL leupeptin, and phenyl methyl sulfonyl fluoride (PMSF) as a protease inhibitor.

The cells were crushed according to the vortex method, centrifuged under the conditions of 15000 rpm and 4° C. for 30 minutes, and the supernatant was taken as a sample. Quantitative determination of protein was performed according to the Bradford method, and a specified amount of protein was separated by SDS-polyacrylic amide gel electrophoresis. The protein was transferred onto a polyvinylidene difluoride (PVDF) film, blocked for 1 hour at room temperature, with a primary antibody applied overnight at 4° C., and a secondary antibody applied for 1 hour at room temperature. The conditions for each antibody are shown in Table 2.

Thereafter, the PVDF film was soaked in an ECL solution and fluorometric detection was performed using an image capture/analysis system (ChemiDocMP System manufactured by Bio-Rad). The detected bands were converted to numerical values using image processing software (ImageJ). The results are shown in FIGS. 14A and 14B.

TABLE 2

| Antibody | Blocking | 1st antibody | 2nd antibody |
| --- | --- | --- | --- |
| α-SMA | 5%BSA/TBS-T | 3%BSA/TBS-T,x2000 | 3%BSA/TBS-T,x4000(mouse) |
| fibronectin | 5%BSA/TBS-T | 3%BSA/TBS-T,x1000 | 3%BSA/TBS-T,x4000(mouse) |
| GADPH | 5%BSA/TBS-T | 3%BSA/TBS-T,x1000 | 3%BSA/TBS-T,x4000(mouse) |

Figure 14A:
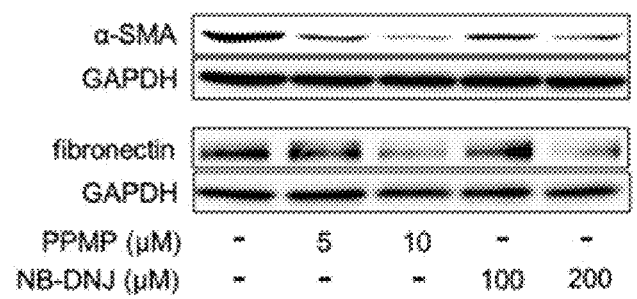
FIG. 14 is western blot images showing the results of expression of αSMA and fibronectin in patient's pulmonary fibroblast cells (FIG. 14A), and a graph showing the αSMA expression levels (FIG. 14B) in Experiment 7.
Figure 14B:
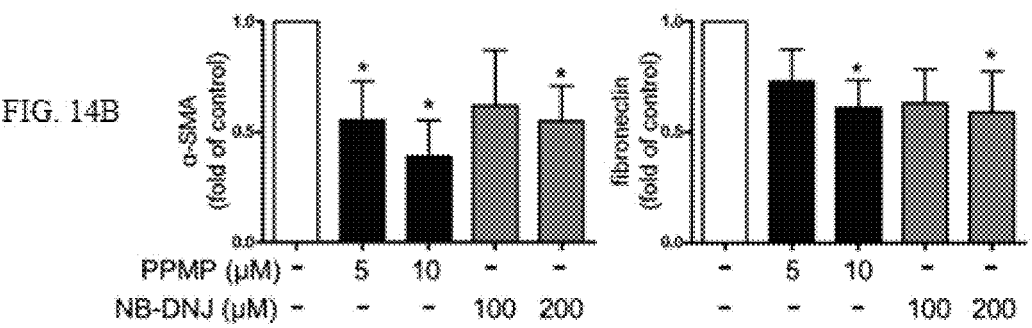

It was confirmed that, in the patient's pulmonary fibroblast cells, the expression of αSMA is suppressed by PPMP and NB-DNJ (FIGS. 14A and 14B).

Experiment 8: Mouse Models for Bleomycin-Induced Pulmonary Fibrosis

Preparation of Mouse Models

50 μL of 3 mg/kg bleomycin hydrochloride/saline solution (Nippon Kayaku Co., Ltd.) was administered through the bronchial tubes to C57BL/6J mice (male, 8 to 12 weeks old) under tribromoethanol-ether anesthesia, to prepare mouse models for pulmonary fibrosis. 50 μL of saline solution was administered in the same manner to a control group not treated with bleomycin hydrochloride.

Bronchial-Tube-Administration of NB-DNJ

Seven, eight and nine days after the administration of bleomycin, 50 μL of 20 mg/kg NB-DNJ/saline solution was administered into the bronchial tubes of the mice under tribromoethanol-ether anesthesia. 50 μL of saline solution was administered into the bronchial tubes to a control group of mice not administered with NB-DNJ.

Oral-Administration of NB-DNJ

For 7 to 13 consecutive days after the administration of bleomycin, 0.2 mL of 600 mg/kg NB-DNJ/saline solution was orally administered daily (once a day). As control group mice which were not administrated with NB-DNJ, 0.2 mL of saline solution was orally administered.

Isolation of Lung

On the 14th day after the administration of bleomycin, each mouse was subjected to thoracotomy under deep ether anesthesia, and its entire body was perfused with PBS from the left ventricle using a syringe needle, while blood was removed from the lungs through the right ventricle, and the lungs were removed.

Western Blot

As for the mice of the bronchial-tube-administration group, the lungs were shredded in 250 μL of RIPA buffer (150 mM NaCl, 50 mM Tris-HCl, 5 mM EDTA, 5 mM NaF, 10 mM sodium pyrophosphate dibasic, 1% Nonidet P-40, 0.1% sodium dodecyl sulfate, 0.5% sodium deoxycholate, pH 8.0) containing phenyl methyl sulfonyl fluoride (PMSF). Thereafter, the tissues were further pulverized using a homogenizer, and centrifuged at 15000 rpm and 4° C. for 30 minutes.

The cells were crushed according to the vortex method, centrifuged under the conditions of 15000 rpm and 4° C. for 30 minutes, and the supernatant was taken as a sample. Quantitative determination of protein was performed according to the Bradford method, and a specified amount of protein was separated by SDS-polyacrylic amide gel electrophoresis. The protein was transferred onto a polyvinylidene difluoride (PVDF) film, and the αSMA antibodies were blocked for 1 hour at room temperature in the same manner as shown in Table 2 above, with a primary antibody applied overnight at 4° C., and a secondary antibody applied for 1 hour at room temperature.

Thereafter, the PVDF film was soaked in an ECL solution and fluorometric detection was performed using an image capture/analysis system (ChemiDocMP System manufactured by Bio-Rad). The detected bands were converted to numerical values using image processing software (ImageJ). The results are shown in FIG. 15.

Figure 15:
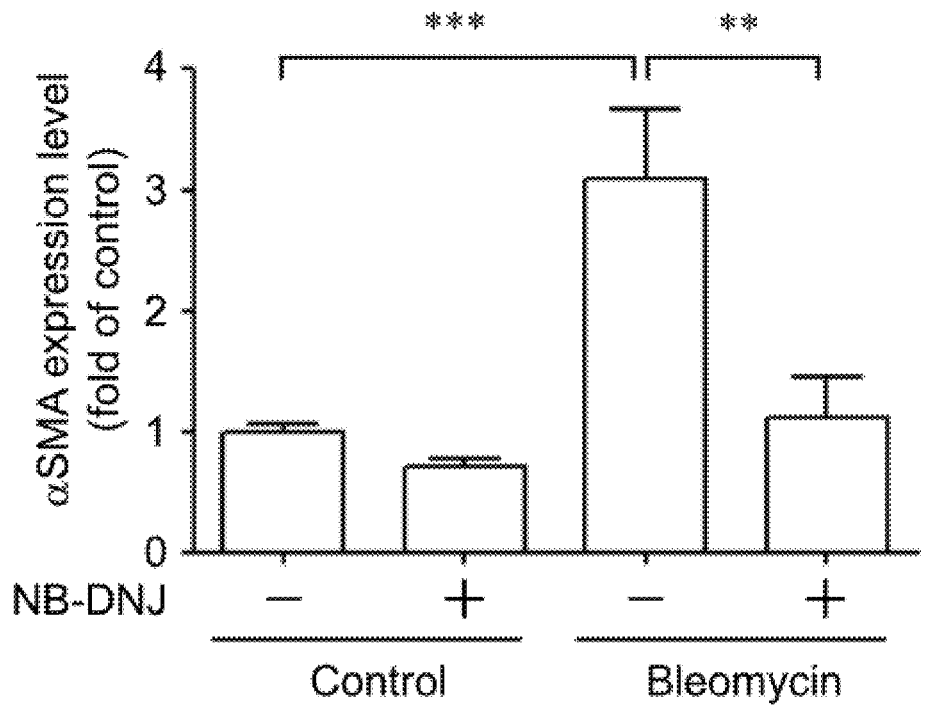
FIG. 15 is a graph showing the αSMA expression levels in Experiment 8.

It was confirmed that bleomycin causes the expression of α-SMA, and that the expression of αSMA is suppressed by NB-DNJ in the presence of bleomycin (FIG. 15).

Preparation of Lung Slices

The lungs were soaked in 4% paraformaldehyde and fixed overnight at 4° C. Thereafter, the lungs were dehydrated for two days in 30% sucrose/PBS solution at 4° C. The tissues were then removed, embedded using an OCT compound, and kept at −80° C. Sections of 5 μm in thickness were prepared using a cryostat, and the sections were mounted on APS-coated glass slides. The glass slides were dried fully, and then kept at 4° C. until they were used in the assay.

Staining with Hematoxylin Eosin

Figure 16:
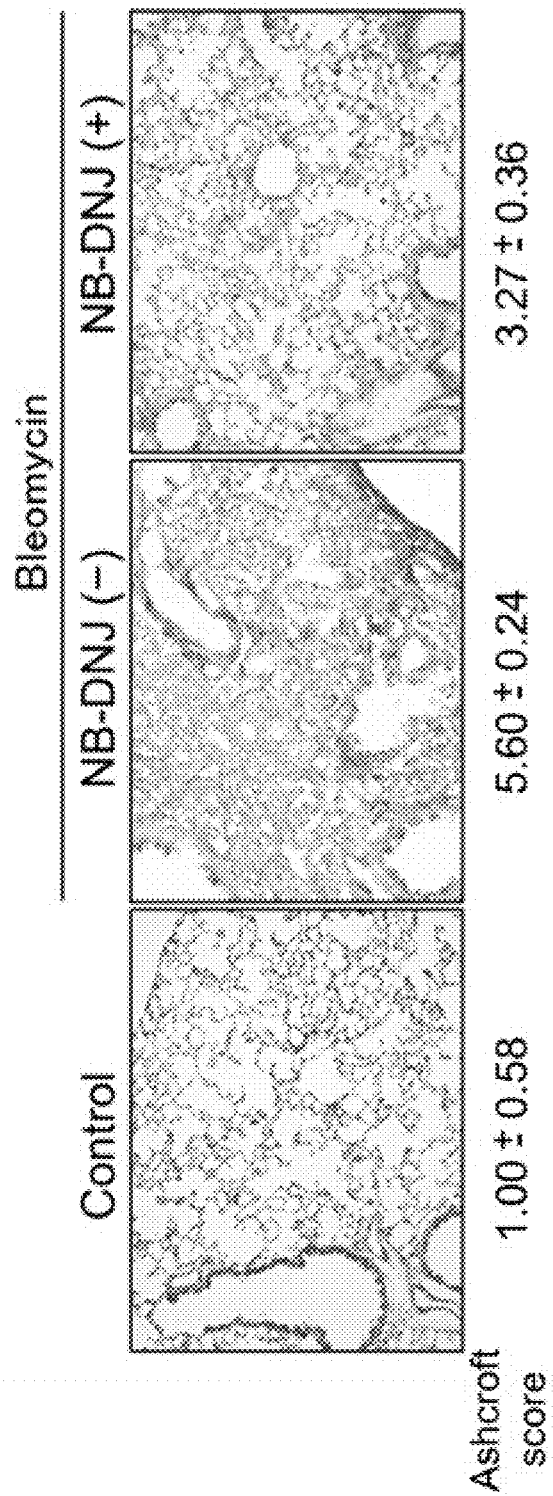
FIG. 16 is Ashcroft scores and microscope images of hematoxylin eosin-stained lung slices of a bronchial-tube-administration group in Experiment 8.

The glass slides with the sections mounted on them were soaked in PBS for 10 minutes to wash away the OCT compound. The glass slides were then soaked in 2 g/L Mayer's hematoxylin solution for 30 minutes and then rinsed under running tap water for 5 minutes for dyeing. Thereafter, the glass slides were soaked in 0.2% eosin Y/ethanol solution for 30 minutes. For the purpose of differential staining, the glass slides were decolorized through each of 80% ethanol, 90% ethanol, 100% ethanol, 50% ethanol/50% xylene, and 100% xylene five times, and then coverslipped with glass covers using Eukit solution. It should be noted that the hematoxylin eosin staining method is used for observing the morphology of tissues, with hematoxylin staining the cell nucleus and eosin staining the cytoplasm. The microscope images and Ashcroft scores of the stained lung sections of the bronchial-tube-administration group are shown in FIG. 16. Also, the microscope images of the stained lung sections of the oral-administration group are shown in FIG. 17.

Figure 17:
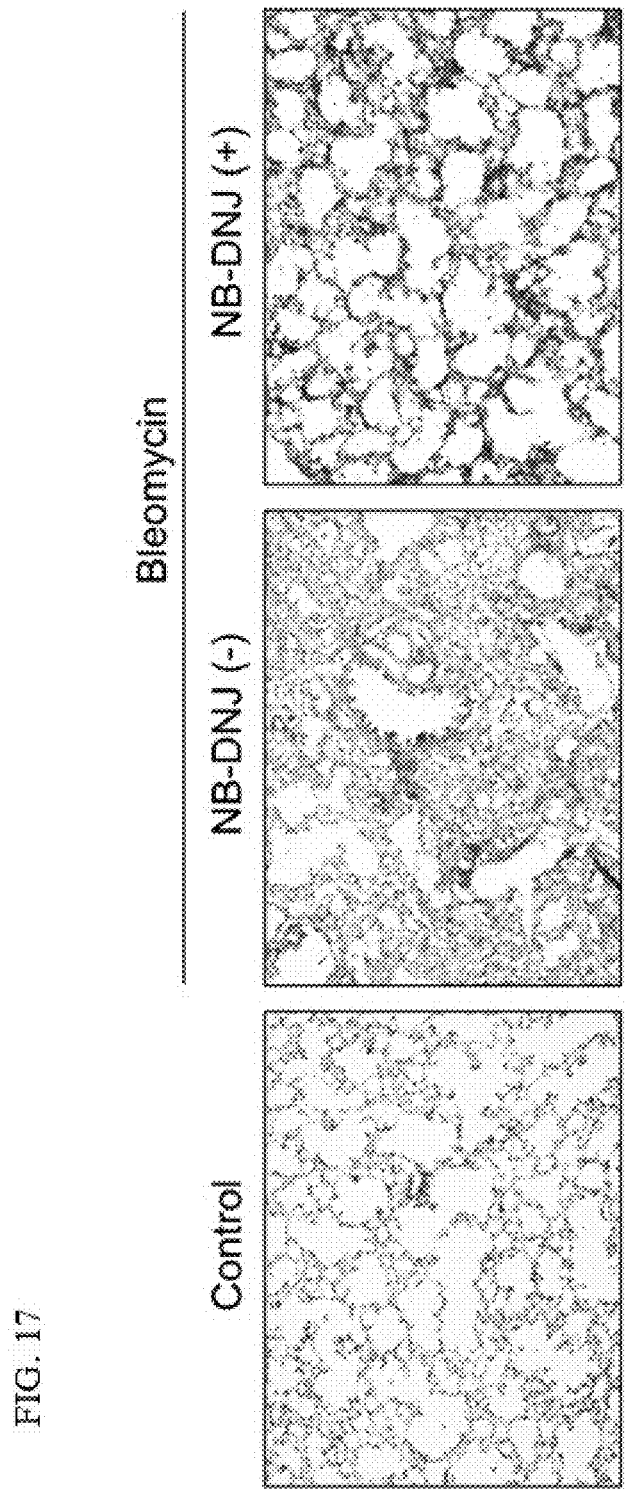
FIG. 17 is microscope images of hematoxylin eosin-stained lung slices of an oral-administration group in Experiment 8.

It was confirmed that the bronchial-tube-administration and oral administration of NB-DNJ suppress the bleomycin-induced fibrosing of the lung (FIGS. 16 and 17). Based on this, NB-DNJ presumably demonstrates anti-fibrotic action by inhibiting Smad signals.

In the present disclosure where conditions and/or structures are not specified, a skilled artisan in the art can readily provide such conditions and/or structures, in view of the present disclosure, as a matter of routine experimentation. Also, in the present disclosure including the examples described above, any ranges applied in some embodiments may include or exclude the lower and/or upper endpoints, and any values of variables indicated may refer to precise values or approximate values and include equivalents, and may refer to average, median, representative, majority, etc. in some embodiments. Further, in this disclosure, "a" may refer to a species or a genus including multiple species, and "the invention" or "the present invention" may refer to at least one of the embodiments or aspects explicitly, necessarily, or inherently disclosed herein. The terms "constituted by" and "having" refer independently to "typically or broadly comprising", "comprising", "consisting essentially of", or "consisting of" in some embodiments. In this disclosure, any defined meanings do not necessarily exclude ordinary and customary meanings in some embodiments.

The present application claims priority to Japanese Patent Application No. 2016-134880, filed Jul. 7, 2016, and No. 2017-131587, filed, Jul. 5, 2017, the disclosure of which is incorporated herein by reference in its entirety including any and all particular combinations of the features disclosed therein.

It will be understood by those of skill in the art that numerous and various modifications can be made without departing from the spirit of the present invention. Therefore, it should be clearly understood that the forms of the present invention are illustrative only and are not intended to limit the scope of the present invention.

We claim:

1. A method for treating fibrosis caused by nuclear translocation of phosphorylated Smad, wherein the fibrosis is idiopathic pulmonary fibrosis, comprising administrating a therapeutic agent for the fibrosis whose active ingredient is constituted by a glucosylceramide synthase inhibitor or lactosylceramide synthase inhibitor, or both, which inhibitor has the activity of inhibiting nuclear translocation of phosphorylated Smad and is contained in a therapeutically effective amount, said inhibitor(s) being a sole inhibitor or sole inhibitors administrated during and for treatment of the fibrosis.

2. A method according to claim 1, wherein the glucosylceramide synthase inhibitor is one or more substance(s) selected from the group consisting of 1-phenyl-2-hexadecanoyl amino-3-morpholino-1-propanol (PPM)), 1-phenyl-2-decanoyl amino-3-morpholino-1-propanol (PDMP), N-butyl deoxynojirimycin (miglustat, NB-DNJ), N-butyl deoxygalactonojirimycin (NB-DGJ), deoxynojirimycin (DNJ), and N-[(1R,2R)-1-(2,3-dihydrobenzo[b][1,4] dioxine-6-yl)-1-hydroxy-3-(pyrrolidine-1-yl) propane-2-yl] octane amide hemi-(2R,3R)-tartrate (Eliglustat tartrate).

3. A method according to claim 1, wherein the lactosylceramide synthase inhibitor is one or more substances selected from the group consisting of N-dodecyl deoxynojirimycin, nojirimycin sulfite adduct, nojirimycin sulfite adduct hydrophobic derivative, and salts thereof.

* * * * *

UNITED STATES PATENT AND TRADEMARK OFFICE
CERTIFICATE OF CORRECTION

PATENT NO. : 10,478,427 B2
APPLICATION NO. : 15/641805
DATED : November 19, 2019
INVENTOR(S) : Hiroyuki Nakamura and Toshihiko Murayama Page 1 of 1

It is certified that error appears in the above-identified patent and that said Letters Patent is hereby corrected as shown below:

In the Claims

At Column 16, Line 9, in Claim 2, please delete "(PPM))" and insert therefor --(PPMP)--

Signed and Sealed this
Twenty-sixth Day of May, 2020

Andrei Iancu
*Director of the United States Patent and Trademark Office*